(12) United States Patent
Pennemann et al.

(10) Patent No.: US 10,155,720 B2
(45) Date of Patent: Dec. 18, 2018

(54) METHOD FOR PRODUCING TOLUENEDIAMINE

(71) Applicant: Covestro Deutschland AG, Leverkusen (DE)

(72) Inventors: Bernd Pennemann, Bergisch Gladbach (DE); Antoni Mairata, Düsseldorf (DE); Antonia Zock, Neuss (DE)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 0 days.

(21) Appl. No.: 15/310,215

(22) PCT Filed: May 11, 2015

(86) PCT No.: PCT/EP2015/060281
§ 371 (c)(1),
(2) Date: Nov. 10, 2016

(87) PCT Pub. No.: WO2015/173161
PCT Pub. Date: Nov. 19, 2015

(65) Prior Publication Data
US 2017/0144963 A1 May 25, 2017

(30) Foreign Application Priority Data

May 13, 2014 (EP) .................... 14168032

(51) Int. Cl.
*C07C 209/36* (2006.01)
*C07C 201/08* (2006.01)
*C07C 201/16* (2006.01)
*B01D 17/04* (2006.01)
*B01D 17/06* (2006.01)

(52) U.S. Cl.
CPC .......... *C07C 209/36* (2013.01); *B01D 17/045* (2013.01); *B01D 17/06* (2013.01); *C07C 201/08* (2013.01); *C07C 201/16* (2013.01); *B01D 2257/80* (2013.01); *Y02P 20/582* (2015.11)

(58) Field of Classification Search
None
See application file for complete search history.

(56) References Cited

U.S. PATENT DOCUMENTS

| 3,162,510 A | 12/1964 | Meissner et al. |
| 3,356,728 A | 12/1967 | Cimerol et al. |
| 4,190,510 A | 2/1980 | Larbig |
| 4,720,326 A | 1/1988 | Beckhaus et al. |
| 4,792,626 A | 12/1988 | Becher et al. |
| 5,001,286 A | 3/1991 | Witt et al. |
| 5,563,296 A | 10/1996 | Zarnack et al. |
| 6,350,911 B1 | 2/2002 | Sander et al. |
| 6,395,934 B1 | 5/2002 | Wegener et al. |
| 6,528,690 B2 | 3/2003 | Klingler et al. |
| 7,326,816 B2 * | 2/2008 | Knauf ................. C07C 201/08 204/450 |
| 7,511,176 B2 | 3/2009 | Pohl et al. |
| 7,517,829 B2 | 4/2009 | Zechlin et al. |
| 9,012,700 B2 | 4/2015 | Knauf et al. |
| 2008/0146847 A1 * | 6/2008 | Pohl ..................... C07C 209/36 564/419 |
| 2009/0005598 A1 * | 1/2009 | Hassan ................ C07C 209/36 564/420 |

FOREIGN PATENT DOCUMENTS

EP 1484312 A1 12/2004

OTHER PUBLICATIONS

Berzak et al. Paschen's Law in Air and Noble Gases, 2006, 1-16.*
Ulmann's Encyclopedia of Technical Chemistry; 4th edition, vol. 7, p. 393 ff, 1973, Verlag Chemie Weinheim/New York.
Kirk-Othmer Encyclopedia of Chemical Technology (4th ed.), vol. 2 (1996) at p. 483-484 and at p. 489-493.
Kirk-Othmer Encyclopedia of Chemical Technology (4th ed.), vol. 17 (1996) at p. 134.
M. Gattrell and B. Louie, Adiabatic Nitration for Mononitrotoluene (MNT) Production, Chemistry, Process Design, and Safety for the Nitration Industry, Chapter 3, 2013, pp. 27-48, ACS Symposium Series, vol. 1155.

* cited by examiner

*Primary Examiner* — Clinton A Brooks
(74) *Attorney, Agent, or Firm* — Donald R. Palladino

(57) ABSTRACT

The invention concerns a method for producing toluenediamine by hydrogenation of dinitrotoluene in the presence of a catalyst, a dinitrotoluene being used as starting material and being processed by applying an electrical voltage.

15 Claims, 1 Drawing Sheet

METHOD FOR PRODUCING TOLUENEDIAMINE

CROSS-REFERENCE TO RELATED APPLICATIONS

This Application is a National Phase Application of PCT/EP2015/060281, filed May 11, 2015, which claims priority to European Application No. 14168032.2, filed May 13, 2014, each of which being incorporated herein by reference.

FIELD

The invention relates to a process for preparing toluenediamine by hydrogenation of dinitrotoluene in the presence of a catalyst, in which a dinitrotoluene which has been treated by application of an electric potential is used as starting material.

BACKGROUND

Toluenediamines are intermediates for the preparation of tolylene diisocyanates (TDI) which are important intermediates produced on an industrial scale for the preparation of polyurethanes. The preparation of these by catalytic hydrogenation of dinitrotoluenes is known and has been described many times (Ullmann's Enzyklopädie der technischen Chemie, $4^{th}$ edition, volume 7, page 393 ff, 1973, Verlag Chemie Weinheim/New York). The industrial preparation of toluenediamines is carried out predominantly by reaction of a mixture of isomeric dinitrotoluenes (hereinafter also referred to as DNT) obtainable by nitration of toluene by means of nitric acid. Commercial mixtures of isomeric dinitrotoluenes are predominantly prepared as crude DNT using nitric acid in the presence of sulfuric acid as catalyst in a two-stage isothermal nitration process with intermediate formation of the corresponding mononitrotoluenes. They are subsequently worked up in steps following the reaction, predominantly in scrubs, and thus largely freed of dissolved sulfuric and nitric acid contents and also of secondary components formed in the reaction stages, e.g. cresols and degradation products thereof.

The catalytic hydrogenation of commercial DNT products can be carried out with concomitant use of an inert solvent or in bulk, with the mixtures then being melted before carrying out the hydrogenation. It can be carried out either batchwise or continuously using conventional reactors. The economic success of the process employed depends substantially on not only a continuous reaction but especially also the selectivities of the reaction which can be achieved in the process employed and also the capacities and operating lives of the catalysts used.

U.S. Pat. No. 3,356,728 discloses an improved continuous process for preparing aromatic amines by catalytic hydrogenation of aromatic polynitroaromatics in a slurry phase reactor, with the process being described by way of example for the reaction of dinitrotoluene. According to the teaching of U.S. Pat. No. 3,356,728, the catalytic hydrogenation of dinitrotoluene in this reaction system is particularly effective in terms of selectivity, catalyst operating life and throughput when the reaction zone is always saturated with hydrogen during the reaction, the aromatic polynitro compound is introduced into the system with maintenance of a particular weight ratio to the catalyst present in the reaction system ("catalyst loading") and the concentration of the aromatic polynitro compound introduced does not exceed a prescribed limit value in the reaction zone.

According to the teaching of U.S. Pat. No. 3,356,728, the catalyst loadings claimed lead to high concentrations of active catalyst in the reaction system, so that the aromatic polynitro compound fed in is immediately converted into the desired amine after being introduced into the mixture, as a result of which the concentration of unreduced nitro compound in the reaction system is kept below 0.005% by weight at all times. According to the teaching of U.S. Pat. No. 3,356,728, rapid poisoning of the catalyst is prevented by this low concentration, and higher yields and an improved product purity combined with significantly reduced costs are also obtained in the reaction of the aromatic polynitro compound. The document does not disclose that the catalyst consumption can be reduced by the DNT to be hydrogenated being subjected to a particular treatment with application of an electric potential.

WO 02/062729 A2 is concerned with improving the mass transfer processes in heterogeneously catalyzed hydrogenation reactions, for example the preparation of aromatic amines from the corresponding nitro compounds. A higher hydrogen saturation of the liquid phase in the reactor is said to be achieved by means of a particular proportion of inert gas in the hydrogenation hydrogen and is said to prevent increased aging of the hydrogenation catalyst and unsatisfactory selectivity of the reaction. Finally, it is also an objective of this publication to ensure very complete conversion of the nitro compound into the amine in the hydrogenation reactor.

SUMMARY

There is a need for processes for reducing the catalyst consumption in the hydrogenation further.

It has now surprisingly been found that the catalyst consumption in the preparation of toluenediamine by reaction of dinitrotoluene with hydrogen in the presence of a catalyst can be reduced when a dinitrotoluene which has been treated by application of an electric potential is used as starting material. The treatment according to the invention leads to a DNT which behaves advantageously in the subsequent hydrogenation thereof.

The present invention accordingly provides a process for preparing toluenediamine by hydrogenation in the presence of a catalyst of a dinitrotoluene starting material which has been treated by application of an electric potential.

DETAILED DESCRIPTION

Figure 1:
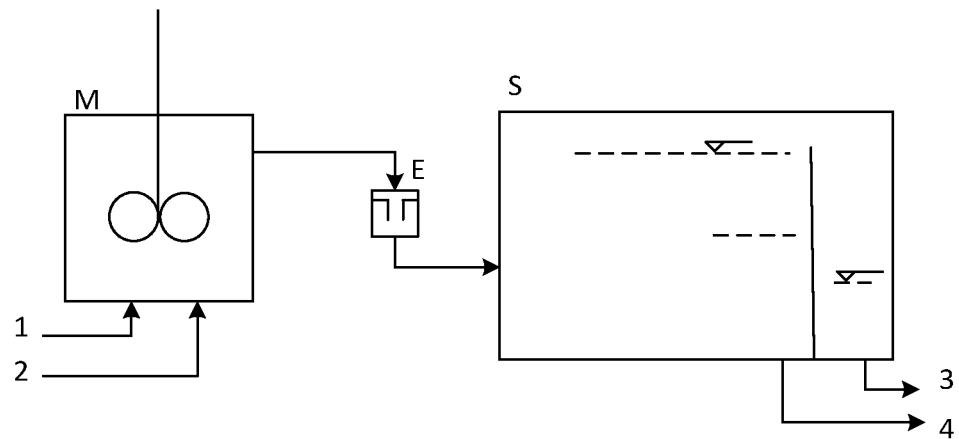
FIG. 1 depicts an embodiment of a unit for carrying out a process according to the invention in which the mixing of dinitrotoluene and aqueous scrubbing medium in the last scrubbing stage of step (ii.2) is followed by an electrocoalescence apparatus for treatment by application of an electric potential in step (iii).

The term toluenediamine (TDA) here encompasses all isomers. TDA isomer mixtures containing, after distillation, from 78% by mass to 82% by mass of 2,4-TDA and from 18% by mass to 22% by mass of 2,6 TDA, in each case based on the total mass of all TDA isomers, are preferably produced by the process of the invention. In the literature, 2,4-TDA and 2,6-TDA are also referred to as meta-TDA.

Various embodiments of the process of the invention are described below. These can be combined with one another in any way, provided that the context does not imply the contrary.

In a preferred embodiment of the process of the invention, the dinitrotoluene starting material treated by application of an electric potential contains from 90% by mass to 99.5% by mass of dinitrotoluene (DNT) and from 0.5% by mass to 10% by mass of water.

The treatment of the DNT by application of an electric potential is preferably carried out by application of a DC voltage of from 50 volt to 1000 volt in a cell having an electrode spacing of from 1 mm to 100 mm, with the dinitrotoluene starting material being subjected to the DC voltage for a period of from 0.01 second to 100 seconds, preferably from 0.1 second to 10 seconds. Here, a current of from 0.1 ampere to 10 ampere is established.

In a further preferred embodiment, the process of the invention comprises the following steps:
(i) dinitration of toluene to form dinitrotoluene;
(ii) work-up of the crude process product obtained in step (i) by (ii.1) removal of the aqueous phase and (ii.2) subsequent at least single-stage scrubbing of the dinitrotoluene phase obtained in (ii.1) by means of at least one aqueous scrubbing medium, where each scrubbing stage comprises mixing of the dinitrotoluene phase with aqueous scrubbing medium and subsequent removal of the aqueous scrubbing medium;
(iii) treatment of the dinitrotoluene by application of an electric potential, where this treatment can be carried out before or after removal of aqueous scrubbing medium used in step (ii);
(iv) hydrogenation of the dinitrotoluene starting material treated by application of an electric potential.

The dinitration of toluene in step (i) can in principle be carried out by all processes known from the prior art. The dinitration is preferably carried out using a mixture of sulfuric acid and nitric acid (nitrating acid). Apart from the single-stage process (EP-A-0 908 442), a two-stage nitration is the generally customary process which is also preferred for the purposes of the present invention. In the two-stage process, toluene is firstly reacted with nitric acid and sulfuric acid to form mononitrotoluene (MNT) (mono stage). Under separation of the resulting reaction mixture into MNT and an acid phase, which can be carried out in static separators or in dynamic separators, the MNT is again reacted with nitric acid and sulfuric acid to form dinitrotoluene (DNT) (di stage). The sulfuric acid phase from the mono stage is concentrated. In the di stage, concentrated sulfuric acid is used. The reaction mixture from the di stage is separated into an organic phase, viz. the crude DNT, and an acid phase, with the acid phase being able to serve as feed sulfuric acid for the mono stage or being passed to concentration. The separation of this reaction mixture from the di stage can likewise be carried out in static or dynamic separators.

In a particularly preferred embodiment, the two-stage process is carried out as follows:
(i.1) toluene is reacted with nitrating acid with maintenance of a mass ratio of aqueous phase to organic phase of >2, preferably >3, very particularly preferably >3.5, and with dispersion of the organic phase in the aqueous phase to form mononitrotoluene, giving a mononitrotoluene-containing reaction mixture;
(i.2) the mononitrotoluene-containing reaction mixture is separated into a mononitrotoluene-containing organic phase and a sulfuric acid-containing aqueous phase;
(i.3) the mononitrotoluene-containing organic phase is reacted with nitrating acid with maintenance of a mass ratio of aqueous phase to organic phase of >1.5 preferably >3, very particularly preferably >3.5, and with dispersion of the organic phase in the aqueous phase, giving a dinitrotoluene-containing reaction mixture;
(i.4) the dinitrotoluene-containing reaction mixture is separated into a dinitrotoluene-containing organic phase and a sulfuric acid-containing aqueous phase;
where a total of less than 2.06 mol of nitric acid are used per mole of toluene.

In steps (i.1) and (i.3), the input of mixing or dispersing energy is preferably selected so that, firstly, the desired dispersions having very large phase interfaces are produced and, secondly, formation of stable "droplets in droplets" emulsions is avoided. The mixing or dispersing energy which is advantageously to be introduced in the reaction steps can easily be determined in simple tests. The maintenance of the phase ratios according to the invention is also dependent on the selected reactor and stirrer geometry and the physical data of the reaction mixtures. However, once the state of the dispersions present in the reaction system has been set, it can advantageously be monitored via the conductivity of the homogeneously mixed reaction mixtures.

The reaction in step (i.1) and/or the step (i.3) is preferably carried out isothermally.

In a preferred embodiment, the reaction in reaction steps (i.1) and (i.3) is in each case carried out in cascades of reactors in which mixing takes place, particularly preferably in cascades each having from 2 to ≤4 reactors. In a particularly preferred embodiment, loop reactors comprising circulation pumps and heat exchangers are used as reactors.

In a very particularly preferred variant, two loop reactors which contain circulation pumps and heat exchangers and are connected in series are used in the monotriation stage. In the dinitration stage, the two loop reactors which comprise circulation pumps and heat exchangers and are connected in series are then used together with a further loop reactor which comprises a circulation pump but no heat exchanger. Here, the circulation pumps are dimensioned so that dispersion of the organic phase in the homogeneous aqueous phase always occurs. In this embodiment, a conductivity measurement is preferably additionally carried out in at least one of the reactors used in order to continuously monitor the state of the circulated dispersion.

The reaction steps (i.1) and (i.3) are each followed by a phase separation step (i.2) and (i.4). Here, it is possible to use all apparatuses suitable for phase separation. Both dynamic and static separators are suitable. In a preferred embodiment, static separators are used in both stages (steps (i.2) and (i.4)).

In the preferred embodiment, the toluene is fed to the mononitration stage in step (i.1). The toluene is preferably introduced into the first reactor, but splitting of the introduction of toluene over a plurality of reactors is likewise possible. The toluene fed into the first reactor is preferably introduced as a mixture with the nitrating acid via one or more nozzles into the reactor. Here, the aqueous phase containing sulfuric acid from step (i.4) (waste acid from the dinitration stage) is preferably mixed beforehand with nitric acid so as to produce the nitrating acid. However, it is also possible to use fresh sulfuric acid or a mixture of fresh sulfuric acid and the waste acid from the dinitration stage.

Separate introduction of the toluene and of the nitrating acid is likewise possible. The separate introduction of the nitric acid and of the sulfuric acid, e.g. the waste acid from the dinitration stage, is likewise possible. The mass ratio of the phases in the reactors of the mononitration stage is preferably set via the amount of sulfuric acid, e.g. the waste acid from the dinitration stage, fed into the reactors. However, recirculation of the sulfuric acid-containing aqueous phase obtained in step (i.2) from the mononitration stage is also possible, with the recirculated sulfuric acid-containing aqueous phase preferably being fed into the first reactor of the stage.

However, introduction over a plurality of reactors of the stage is likewise possible. Splitting of the nitric acid introduced in the mononitration over a plurality of reactors is also possible.

The reaction of the toluene in the mononitration stage (step (i.1)) is preferably carried out in a temperature range from 30° C. to 70° C., with the reactors of mononitration stage being able to be operated at the same reaction temperature. However, different reaction temperatures in the individual reactors matched to the progress of the reaction are likewise possible.

The dispersions present in the reactors of the mononitration stage (step (i.1)) are preferably monitored continuously by means of conductivity measurements. In this way, unacceptable deviations, which are recognizable, for example, from a significant decrease in the conductivity of the circulated reaction mixtures, from changes in the mixing energy introduced via the mixing and dispersing devices into the reactors or preferably from a change in the phase ratio in the reactors of the nitration stage, are corrected.

In the above-described embodiment of step (i), a very high toluene conversion is achieved with very effective utilization of the nitric acid fed into the mononitration stage. The sulfuric acid-containing aqueous phase (waste acid) obtained in the subsequent phase separation typically has nitric acid contents of <0.1% by mass, based on the total mass of the waste acid. These low contents lead to the very low specific nitric acid consumption of this process. In addition, they reduce the outlay necessary for concentrating the waste acid from the mononitration stage.

In the preferred embodiment of step (i), the organic phase obtained in the phase separation of the mononitration stage (step (i.2)) is preferably fed without further work-up into the reactors of the dinitration stage (step (i.3)). The MNT-containing organic phase is preferably fed into the first reactor, but splitting the introduction over a plurality of reactors is likewise possible. The MNT fed into the first reactor is preferably introduced as a mixture with the nitrating acid via one or more nozzles into the reactor. Preference is given to the sulfuric acid-containing aqueous phase from step (i.2) (waste acid from the mononitration stage) optionally being worked up and mixed with nitric acid beforehand so as to produce the nitrating acid. However, fresh sulfuric acid or a mixture of fresh sulfuric acid and the waste acid from the mononitration stage can also be used. Separate introduction of the MNT-containing organic phase from step (i.2) and the nitrating acid is likewise possible. The separate introduction of the nitric acid and of the sulfuric acid, e.g. the treated waste acid from the mononitration stage, is likewise possible. The weight ratio of the phases in the reactors of the dinitration stage (step (i.3)) is preferably set via the amount of the sulfuric acid, e.g. the treated waste acid from the mononitration stage, fed into the reactors. However, recirculation of the sulfuric acid-containing aqueous phase from the dinitration stage obtained in step (i.4) is also possible, with the recirculated sulfuric acid-containing aqueous phase preferably being fed into the first reactor of the stage. However, introduction over a plurality of reactors of the stage is likewise possible. Splitting of the nitric acid fed to the dinitration over a plurality of reactors is also possible.

The reaction of the mononitrotoluene in the dinitration stage (step (i.3)) is carried out in a temperature range from 55° C. to 80° C., with the reactors of the dinitration stage being able to be operated at the same reaction temperature. However, different reaction temperatures in the individual reactors matched to the progress of the reaction are likewise possible.

The dispersions present in the reactors of the dinitration stage (step (i.3)) are preferably monitored continuously by means of conductivity measurements. Unacceptable deviations, which can be recognized, for example, from a significant decrease in the conductivity of the recirculated reaction materials, from changes in the mixing energy introduced via the mixing or dispersing devices into the reactors or else preferably from a change in the phase ratio in the reactors of the nitration stage, are thus corrected.

In the preferred embodiment of step (i), a very high mononitrotoluene conversion is achieved with very effective utilization of the nitric acid fed into the dinitration stage. The sulfuric acid-containing aqueous phase (waste acid) obtained in the subsequent phase separation typically has nitric acid contents of <0.2% by mass, based on the total mass of the waste acid. The loadings of the DNT-containing organic phase obtained in step (i.4) with nitric acid are <0.4% by mass of $HNO_3$, based on the mass of the organic phase. This embodiment of step (i) is described in EP-A-1 880 989.

In all processes for preparing DNT by nitration of toluene by means of nitrating acid, a crude process product is obtained and is worked in a further step (ii). For this purpose, the aqueous phase is firstly separated off (step (ii.1), which can occur in phase separation apparatuses known to those skilled in the art. This leaves an organic, DNT-containing phase (hereinafter also referred to as crude DNT) which can, depending on the precise reaction and separation conditions, still contain up to 5% by mass, preferably up to 1.2% by mass, of nitric acid and up to 6% by mass, preferably up to 1.5% by mass, of sulfuric acid. In addition, by-products of the nitration are present in a concentration of up to about 1% by mass. The by-products are mainly nitrocresols, picric acid and nitrobenzoic acids.

This crude DNT obtained by simple phase separation can be scrubbed directly in step (ii.2). However, it is also possible and particularly preferred in the case of high residual contents of acids for an aqueous phase containing sulfuric acid and nitric acid to be separated off beforehand from this crude DNT. For this purpose, the crude DNT obtained by simple phase separation is mixed with up to 10% by mass of water, preferably from 0.3% by mass to 8% by mass, based on the total mass of the crude DNT, preferably at a temperature of from 65° C. to 95° C. Here, an aqueous phase containing sulfuric acid and nitric acid separates out and is separated off. It is also possible for this operation to be carried out in two stages by firstly mixing the crude DNT obtained by simple phase separation with from 0.3% by mass to 3% by mass of water, based on the total mass of the crude DNT, separating off the aqueous phase containing predominantly sulfuric acid which separates out and subsequently mixing the remaining organic phase with from 2% by mass to 6% by mass of water, based on the total mass of this organic phase, and separating off the phase containing predominantly nitric acid which separates out. This embodiment of step (ii.1) is described in EP-A-0 279 312.

The DNT-comprising phase obtained in step (ii.1) is subjected to a scrub with at least one aqueous scrubbing medium in step (ii.2). This scrub can in principle be carried out in a manner known from the prior art.

In a preferred embodiment, the DNT-comprising phase is freed of acid and secondary components in from 2 to 4 scrubbing stages using an aqueous scrubbing medium. The aqueous scrubbing medium fed into this process can contain a base in at least one scrubbing stage, with use usually being made of sodium hydroxide or sodium carbonate in concentrations of from 2 to 10% by mass. The base is preferably not used in the last scrubbing stage, i.e. neutral water is preferably used for the last scrubbing stage. While sulfuric acid and nitric acid are largely removed from the nitration product by the neutral water scrub, the alkaline scrub also transfers salt-forming organic components such as nitrocresols, picric acid and nitrobenzoic acids into the aqueous phase.

As aqueous scrubbing medium, it is possible to use, except in the last scrubbing stage, scrubbing water conveyed in countercurrent from a subsequent stage. The scrubbing water used can, however, also be fresh water, demineralized water or water having a suitable quality from a downstream process of the nitration process described.

The amounts of scrubbing water used are preferably from 15 to 90 parts by weight, particularly preferably from 50 to 65 parts by weight, of scrubbing water per 100 parts by weight of DNT.

The scrub in step (ii.2) particularly preferably comprises from 3 to 4 stages. Here, neutral or slightly acidic water (e.g. from aqueous recycle streams of the nitration process or the associated concentration of sulfuric acid) is preferably used as aqueous scrubbing medium in the first scrubbing stage. In this scrubbing stage, an acidic process wastewater having preferred acid contents of from 1.0 to 3.0% by mass of nitric acid and from 2.0 to 6.0% by mass of sulfuric acid and a DNT content of some 1000 ppm is formed, depending on amount of scrubbing water used and the way in which the scrubbing water is conveyed. The concentration of organic by-products of the nitration is generally in the range from 300 to 900 ppm in the abovementioned process wastewater. In the second scrubbing stage, a scrubbing water which has been made alkaline by means of a base (preferably sodium hydroxide or sodium carbonate) is preferably used. From 3.0 to 7.0% by mass of organic by-products of the nitrogenation, mainly nitrocresols, picric acid and nitrobenzoic acids, in the form of their water-soluble salts of the base used are generally present in the wastewater stream from this alkaline scrub. In addition, this wastewater stream can also contain a number of 1000 ppm of DNT and also from 2.0 to 4.0% by mass of nitric acid and from about 0.6 to 1.2% by mass of sulfuric acid in the form of their water-soluble salts. The wastewater stream from the alkaline scrub has a pH of >7.0, preferably >7.5 (measured at 80° C.). This alkaline scrub is preferably followed by one or two scrubbing stages using neutral water.

In another embodiment of step (ii.2), the addition of a base is omitted, and the scrub is then carried out in from 2 to 6 stages.

In all embodiments, neutral water is preferably used in the last scrubbing stage.

The scrubbing stages are carried out in suitable apparatuses known to those skilled in the art, preferably in scrubbing or extraction columns or in mixer-settler apparatuses.

The scrub in step (ii.2) is preferably configured as a multistage extraction encompassing mixing and phase separation in each stage. In this preferred embodiment, the extraction in the stages is carried out as a "liquid/liquid" extraction. This is ensured by suitable choice of the temperatures of the DNT-comprising phase used and of the aqueous phases used as extractants.

In a further preferred embodiment, the multistage extraction is, at least in one stage, carried out using an apparatus for mixing and separating liquids which have different specific gravities and are virtually insoluble in one another, as is described, for example, in DE-B-1 135 425.

Characteristics of the apparatus described in DE-B-1 135 425 are a mixing zone which is configured as extraction or scrubbing column and has a space for phase separation which is arranged concentrically around the mixing zone and in which the mixture leaving the mixing zone enters via an overflow weir with surrounding hollow jacket of the "cut-off" scrubbing column and is separated according to the densities into two phases. To use the apparatus whose structure is described in DE-B-1 135 425 in column 2/lines 35-52 and column 3/lines 1-12 and whose function is described in column 3/lines 29-47 in an advantageous manner in the process of the invention, the apparatus should additionally be equipped with a facility for introduction of inter gas (preferably nitrogen) into the mixing zone, for example via an additional opening in the region of the bottom of this section of the apparatus.

However, any form of multistage extraction processes and extraction apparatuses comprising mixing and phase separation in each stage can in principle be used for the scrubbing in step (ii.2), where the residence time for mixing in each stage of the extraction in step (ii.2) is preferably at least 4 minutes and not more than 60 minutes and an inert gas (preferably nitrogen) is preferably additionally introduced into the mixing zone (i.e. into the body in which mixing takes place) at least in the last stage of the extraction in step (ii.2).

In step (iii), the scrubbed DNT-containing phase obtained in step (ii) is treated by application of an electric potential. This is preferably carried out by application of a DC voltage of from 50 volt to 1000 volt in a cell having an electrode spacing of from 1 mm to 100 mm, with the dinitrotoluene starting material being subjected to the DC voltage for a period of from 0.01 second to 100 seconds, preferably from 0.1 second to 10 seconds. A current of from 0.1 to 10 ampere is established here. This treatment is preferably carried out by means of an electrocoalescence apparatus. For the purposes of the present invention, the term electrocoalescence apparatus encompasses an apparatus in which the scrubbed DNT flows through a cell whose electrodes are connected to a voltage source. The cell can, for example, have plate-like or cylindrical electrodes. In the case of plate-like electrodes, at least two right-angled electrodes which are arranged parallel to one another are usually selected. If more than two electrodes are used, these are advantageously connected alternately to the voltage source. The electrode arrangement is placed in an apparatus or container, with one of the electrodes itself also being able to be the container wall. Examples of suitable electrocoalescence apparatuses are the "electrophoresis units" described in EP-A-0 004 278 and EP-A-1 816 117.

The treatment according to the invention of the DNT by application of an electric potential is preferably carried out in or after the last scrubbing stage of step (ii.2). This can occur by the mixing of dinitrotoluene and aqueous scrubbing medium in the last scrubbing stage of step (ii.2) (which is preferably carried out using neutral, i.e. neither basified nor acidified, water) being followed by an electrocoalescence apparatus for treatment by application of an electric potential in step (iii). A static or dynamic mixer (preferably comprising one or more stirrers or a pump, particularly preferably a centrifugal pump) can be used in the last scrubbing stage. A dynamic mixer which is preferably provided with one or more stirrers is preferably used in this embodiment of step (ii.2). Mixing by mean of a stirrer has the advantage that a sufficient mixing performance is achieved even at relatively small throughputs. This embodiment is depicted in FIG. 1. Here, 1 is the DNT stream, 2 is a stream of introduced scrubbing water, 3 is the discharged scrubbing water and 4 is the DNT which has been freed of impurities. M denotes the mixing device, E the electrocoalescence apparatus and S the phase separation apparatus. In M, the DNT 1 which has preferably been scrubbed in preceding stages of step (ii) is mixed with (preferably neutral) scrubbing water 2. The DNT/water mixture obtained flows through the electrocoalescence apparatus E before being separated in the phase separation apparatus S into an aqueous phase 3 (discharged scrubbing water) and an organic phase 4 (the DNT starting material which has been treated by application of an electric potential). The arrangement shown in FIG. 1 is naturally also able to be realized when using a static mixer. To implement the process of the invention in an existing DNT production plant, the mixer of the existing last scrubbing stage can be used as mixer M. However, it is likewise possible to install an arrangement as shown in FIG. 1 as combined scrubbing and electrocoalescence apparatus downstream of the existing last scrubbing stage.

Figure 2:
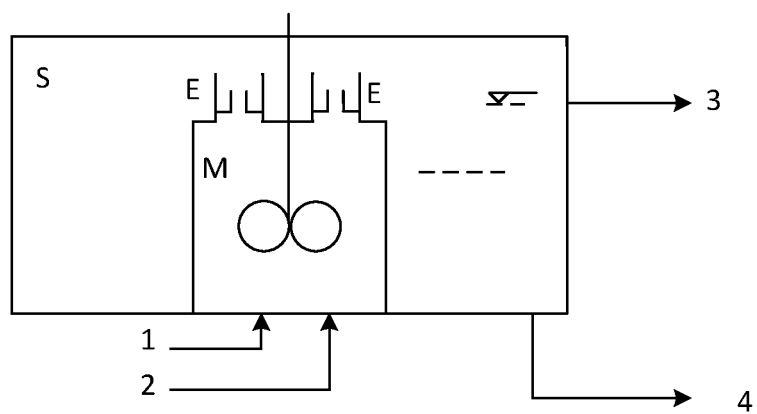
FIG. 2 depicts an embodiment of a unit for carrying out a process according to the invention in which an electrocoalescence apparatus is integrated into the mixing of dinitrotoluene and aqueous scrubbing medium of the last scrubbing stage of step (ii.2).

It is likewise possible to integrate the electrocoalescence apparatus into the mixing of DNT phase and aqueous scrubbing medium of the last scrubbing stage of step (ii.2), i.e. to arrange the electrocoalescence apparatus in the mixer of the last scrubbing stage. In a preferred variant of this embodiment, a mixing zone, an electrocoalescence apparatus and a settling zone are combined in one apparatus which is divided into a plurality of zones. Here, the mixing zone in which DNT and scrubbing water are mixed is preferably located inside and the settling zone in which the aqueous phase and the DNT phase are separated is preferably located outside. Mixing of DNT and scrubbing water can be carried out by means of dynamic mixers (e.g. one or more stirrers, a pump, preferably a centrifugal pump) or static mixers. Dynamic mixers are preferred in this embodiment, too. FIG. 2 shows a corresponding arrangement.

It is also possible to build the electrocoalescence apparatus into a settling tank for DNT which is located downstream of the phase separation apparatus of the last scrubbing stage in step (ii.2) (which is preferably carried out using neutral, i.e. neither basified nor acidified, water) for taking up the scrubbed DNT which has been separated from the scrubbing water or into a pipe which connects the phase separation apparatus of the last scrubbing stage to the settling tank. Particularly when the electrocoalescence apparatus is arranged in the settling tank, it can be advantageous for water to be fed in addition to the scrubbed dinitrotoluene-comprising phase into the settling tank and to take an aqueous phase which separates out from the settling tank, preferably discontinuously. In this way, any by-products which interfere in the hydrogenation can be discharged with the aqueous phase.

When the electrocoalescence apparatus is arranged in the settling tank or a pipe connecting the last scrubbing stage to the settling tank, preference is also given to using a dynamic mixer in the last scrubbing stage of step (ii.2).

In each case, the operation of separation of DNT and water can be assisted by suitable internals with which a person skilled in the art would be familiar in the phase separation apparatus, for example plates, knitted fabrics or porous shaped bodies such as filter candles.

The DNT starting material which has been treated by application of an electric potential obtained in step (iii) is hydrogenated to toluenediamine (TDA) in step (iv). This hydrogenation can in principle be carried out by any process known from the prior art. Preference is given to proceeding as follows:

The DNT starting material which has been treated by application of an electric potential obtained in step (iii) is preferably collected in a receiver and from this fed in liquid form to the hydrogenation which is preferably operated continuously. The dinitrotoluenes which preferably flow continuously into the receiver can be subjected to a stripping gas treatment using an inert gas either before collection in the receiver, in the receiver or after being taken from the receiver. The catalytic hydrogenation of the DNT starting material can be carried out with concomitant use of an inert solvent or in bulk. It is preferably carried out in bulk using an aqueous catalyst suspension. It can be carried out either batchwise or continuously using conventional reactors. Examples of such reactors are stirred vessels, bubble columns or loop reactors such as loop-Venturi reactors or jet loop reactors having an internal circuit and an external circuit.

The introduction of hydrogen into the system is preferably carried out in such a way that the stoichiometric requirement of hydrogen for the reaction of the nitro group equivalents fed in to the corresponding amine compounds is always covered and, in addition, the content of the reactor is always saturated with hydrogen, taking particular account of the surface areas of the catalyst used.

As catalysts, it is possible to use all hydrogenation catalysts known for the catalytic hydrogenation of aromatic nitro compounds in step (iv). The metals of transition group 8 of the Periodic Table of the Elements or mixtures of these and also copper are particularly well suited. The catalyst is particularly preferably selected from among catalysts containing Pt, Pd, Rh, Ru, Ni, Co, Cu and mixtures thereof; the catalyst is used here in a concentration of from 0.01% by mass to <20% by mass, based on the total mass of the reaction mixture in the hydrogenation. The catalysts can, for example, have been applied to support materials such as carbon or oxides of magnesium, aluminum and/or silicon. In a further embodiment of the process of the invention, Raney iron, Raney cobalt and/or Raney nickel, in particular nickel-containing catalysts such as Raney nickel catalysts, and also palladium- or platinum-containing catalysts on support materials are used; the preparation and use of these as hydrogenation catalyst for aromatic nitro compounds such as nitrobenzene, nitrotoluenes, dinitrotoluenes, chlorinated nitroaromatics and others is known and has been described a number of times (EP 0 223 035 B1, EP 1 066 111 B1, EP-A-1 512 459).

In a very particularly preferred embodiment of the process of the invention, Raney nickel catalysts as are described in EP-A-1 512 459 are used as catalysts. Compared to conventional Raney nickel catalysts, these catalysts display a significantly increased product selectivity and catalyst operating life, especially at reaction temperatures of >120° C.

Their use can sometimes enable the heat of reaction liberated in the hydrogenation of dinitrotoluenes to be utilized particularly advantageously for generating steam which can be used as heating medium.

The reaction mixture is taken off from the reaction system for the catalytic hydrogenation of the dinitrotoluenes, which is preferably operated continuously, in an amount corresponding to that fed in, preferably continuously while retaining the catalyst in the system. The reaction mixture is particularly preferably taken off using a crossflow filtration as is, for example, described in principle in EP 0 634 391 B1 or in a specific embodiment in EP 1 137 623 B1. In this way of discharging the product, a substream is taken from the reactor and conveyed over a crossflow filter, a substream is taken off there from the product stream with retention of the catalyst, and the smaller substream which has been "concentrated" in respect of its catalyst content is finally returned to the reactor.

Deactivated catalyst can be replaced by fresh catalyst without production necessarily having to be interrupted for this purpose. In the case of a reactor which has sufficiently large dimensions, fresh catalyst can be fed in over a long period of time without exhausted catalysts being removed. It is naturally also possible to configure the reaction in such a way that exhausted catalyst is discharged continuously or periodically, so that production can theoretically continue without interruption. In either case, the process of the invention displays a low catalyst consumption.

The filtered product has a high purity and can be worked up without further chemical after-treatment according to the prior art to give the end product toluenediamine (TDA). According to the prior art, this work-up comprises removal of water of reaction and, if used, of solvent and purification of the TDA to a purity required for the desired subsequent application, generally (and also preferably for the purposes of the present invention) phosgenation to form tolylene diisocyanate (TDI). The water of reaction is freed of volatile organic impurities. Such a work-up of the TDA-containing process product obtained after filtration can be configured so that water of reaction is firstly separated off by distillation, with the TDA stream obtained in this step and the water stream obtained in this step being purified further in downstream distillation steps. It is likewise possible, as described in EP-A-0 236 839, to carry out removal and purification of the water of reaction in one step. In any case, a stream of water of reaction which has been separated off and purified by distillation is obtained and can either be disposed of as wastewater or passed to another use. EP-A-1 484 312 discloses the use of such water in the scrubbing of crude DNT. In the context of the present invention, too, it is possible for water of reaction from the DNT hydrogenation (step (iv)) which has been separated off and purified by distillation to be used in the scrub of step (ii.2). This also applies to the last scrubbing stage of step (ii.2), in or after which the electrical treatment (iii) takes place in a preferred embodiment of the process of the invention.

EXAMPLES

Example 1 (Comparison)

In a continuously operated reactor for the hydrogenation of DNT, technical-grade DNT is hydrogenated in the presence of an Ni-based catalyst in a proportion by mass of 7%, based on the contents of the reactor, at a pressure of 24 bar (absolute) and a residence time of 1.8 hours. To maintain the reaction, it is necessary to add catalyst on average every 15 hours.

Example 2 (According to the Invention)

A unit as shown in FIG. 1 is started up (except that a static mixer is used instead of the mixer with stirrer as shown). Here, 50 kg of water (2) per t of DNT (1) are mixed in a static mixer M. The DNT-water mixture obtained is treated in an electrocoalescence apparatus E at 400 V for 1 second and the resulting treated mixture is separated from water (3) in a separation apparatus S. The DNT (4) is hydrogenated in the same reactor as also used in example 1 under the same conditions of pressure, type of catalyst and catalyst concentration and also residence time. Now, the addition of fresh catalyst is necessary only on average every 31 hours.

The invention claimed is:

1. A process for preparing toluenediamine by hydrogenation in the presence of a catalyst of a dinitrotoluene starting material which has been treated by application of an electric potential using a DC voltage of from 50 volt to 1000 volt in a cell having an electrode spacing of from 1 mm to 100 mm for a period of from 0.01 second to 100 seconds.

2. The process of claim 1, wherein the dinitrotoluene starting material treated by application of an electric potential contains from 90% by mass to 99.5% by mass of dinitrotoluene and from 0.5% by mass to 10% by mass of water.

3. The process of claim 1, wherein the catalyst is selected from among catalysts containing Pt, Pd, Rh, Ru, Ni, Co, Cu or mixtures thereof and the catalyst is used in a concentration of from 0.01% by mass to <20% by mass, based on the total mass of the reaction mixture in the hydrogenation.

4. A process for preparing toluenediamine, comprising:
   (i) dinitrating toluene to form dinitrotoluene;
   (ii) working-up the crude process product obtained in step (i) by (ii.1) removal of the aqueous phase and (ii.2) subsequent at least single-stage scrubbing of the dinitrotoluene phase obtained in (ii.1) by means of at least one aqueous scrubbing medium, where each scrubbing stage comprises mixing of the dinitrotoluene phase with aqueous scrubbing medium and subsequent removal of the aqueous scrubbing medium;
   (iii) treating the dinitrotoluene by application of an electric potential using a DC voltage of from 50 volt to 1000 volt in a cell having an electrode spacing of from 1 mm to 100mm for a period of from 0.01 second to 100 seconds, where the treatment is carried out before or after removal of aqueous scrubbing medium used in step (ii); and
   (iv) hydrogenating the dinitrotoluene starting material treated by application of an electric potential.

5. The process of claim 4, wherein the scrubbing in step (ii.2) comprises from two to four stages and the aqueous scrubbing medium of at least one of the stages apart from the last stage contains a base.

6. The process of claim 4, wherein the scrubbing in step (ii.2) comprises from 2 to 6 stages and the aqueous scrubbing medium does not contain a base in any of the stages.

7. The process of claim 4, wherein the treatment in step (iii) is carried out by application of an electric potential in or after the last scrubbing stage in step (ii.2).

8. The process of claim 7, wherein the mixing of dinitrotoluene and aqueous scrubbing medium in the last scrubbing stage of step (ii.2) is followed by an electrocoalescence apparatus for treatment of the dinitrotoluene by application of an electric potential in step (iii).

9. The process of claim 7, wherein an electrocoalescence apparatus for treatment of the dinitrotoluene by application of an electric potential in step (iii) is integrated into the mixing of dinitrotoluene phase and aqueous scrubbing medium in the last scrubbing stage of step (ii.2).

10. The process of claim 7, wherein the removal of aqueous scrubbing medium in the last scrubbing stage of step (ii.2) is carried out in a phase separation apparatus having a downstream settling tank for taking up the scrubbed dinitrotoluene phase, where the settling tank or a pipe connecting the settling tank to the phase separation apparatus is provided with an electrocoalescence apparatus for the treatment by application of an electric potential in step (iii).

11. The process of claim 10, wherein water is fed in addition to the scrubbed dinitrotoluene phase into the settling tank and the aqueous phase which settles out is taken off continuously or discontinuously from the settling tank.

12. The process of claim 11, wherein the aqueous phase is taken off discontinuously.

13. A process for preparing toluenediamine comprising:
(a) treating a dinitrotoluene starting material by application of an electric potential using a DC voltage of from 50 volt to 1000 volt used as electric potential to which the dinitrotoluene starting material is subjected in a cell having an electrode spacing of from 1 mm to 100 mm for a period of from 0.01 second to 100 seconds; and
(b) hydrogenating the treated dinitrotoluene starting material in the presence of a catalyst.

14. The process of claim 13, wherein the dinitrotoluene starting material treated by application of an electric potential contains from 90% by mass to 99.5% by mass of dinitrotoluene and from 0.5% by mass to 10% by mass of water.

15. The process of claim 13, wherein the catalyst is selected from among catalysts containing Pt, Pd, Rh, Ru, Ni, Co, Cu or mixtures thereof and the catalyst is used in a concentration of from 0.01% by mass to <20% by mass, based on the total mass of the reaction mixture in the hydrogenation.

* * * * *